United States Patent
Hou et al.

(10) Patent No.: US 10,023,624 B2
(45) Date of Patent: Jul. 17, 2018

(54) LONG-ACTING RECOMBINANT HUMAN FOLLICLE-STIMULATING HORMONE-FC FUSION PROTEIN

(71) Applicant: UnicoMed Pharma Co. Ltd., Guangzhou (CN)

(72) Inventors: Yongmin Hou, Guangzhou (CN); Qiang Li, Guangzhou (CN); Maobo Wu, Guangzhou (CN); Sha Liao, Guangzhou (CN); Yujie Zhang, Guangzhou (CN); Zhenqi Xu, Guangzhou (CN)

(73) Assignee: UnicoHealth Co. Ltd., Guangzhou, Guangdong (CN)

( * ) Notice: Subject to any disclaimer, the term of this patent is extended or adjusted under 35 U.S.C. 154(b) by 0 days.

(21) Appl. No.: 15/033,286

(22) PCT Filed: Aug. 22, 2014

(86) PCT No.: PCT/CN2014/085010
§ 371 (c)(1),
(2) Date: Jul. 18, 2016

(87) PCT Pub. No.: WO2015/062349
PCT Pub. Date: May 7, 2015

(65) Prior Publication Data
US 2017/0174736 A1 Jun. 22, 2017

(30) Foreign Application Priority Data
Nov. 1, 2013 (CN) .......................... 2013 1 0529896

(51) Int. Cl.
*C07K 14/59* (2006.01)
*A61K 38/00* (2006.01)

(52) U.S. Cl.
CPC .............. *C07K 14/59* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,712,122 A * | 1/1998 | Boime | ............ | C07K 14/59 435/320.1 |
| 6,238,890 B1 * | 5/2001 | Boime | ............ | C07K 14/575 435/252.3 |
| 2003/0082679 A1 * | 5/2003 | Sun | ............ | C07K 14/535 435/69.1 |
| 2010/0291079 A1 * | 11/2010 | Low | ............ | C12N 15/62 424/134.1 |

FOREIGN PATENT DOCUMENTS

| | | |
|---|---|---|
| CN | 1131952 A | 9/1996 |
| CN | 102786589 A | 11/2012 |
| CN | 103159860 A | 6/2013 |
| CN | 103539862 A | 1/2014 |
| WO | 2003/064677 A3 | 8/2003 |
| WO | 2005/058953 A2 | 6/2005 |

OTHER PUBLICATIONS

Sugahara et al., JBC, 1996; 271: 10445-10448.*
McCue et al., Methods in Enzymology, vol. 463 # 2009 Elsevier Inc. ISSN 0076-6879, DOI: 10.1016/S0076-6879(09)63025-1: 405-414.*
The Guide on Hydrophobic Interaction Chromatography (Principles and Methods), by Amersham Pharmacia Biotech, Edition AB, ISBN 91-970490-4-2, (1993); 104 pages total. (Year: 1993).*
The MIT doctoral thesis by Lam Raga Anggara Markely (Jun. 2011); 105 pages total. (Year: 2011).*
Translation of Diao, Yao hsüeh hsüeh pao / Yao Xue Xue Bao: vol. 47 Issue: 4; pp. 421-426 Publication Date: 2012; translation is 24 pages total. (Year: 2012).*
Human Reproduction vol. 20, No, 7 pp. 1805-1813, 2005, S.C.Low, Advance Access Publication Apr. 7, 2005, Oral and Pulmonary Delivery of FSH-Fc Fusion Proteins Via Neonatal Fc Receptor—Mediated Transcytosis.
Written Opinion of the International Searching Authority dated Jan. 4, 2015; Appln. No. PCT/CN2014/095585.

* cited by examiner

*Primary Examiner* — Christina M Borgeest
(74) *Attorney, Agent, or Firm* — The Dobrusin Law Firm, PC

(57) ABSTRACT

Recombinant Fc fusion proteins of human follicle-stimulating hormone (hFSH) with in vivo biological activities comparable to those of human follicle-stimulating hormone are disclosed. A recombinant hFSH-Fc fusion protein comprises β subunit of hFSH (hFSH β), CTP, α subunit of hFSH (hFSH α), a flexible peptide linker, and human IgG2 Fc variant (vIgG2Fc). A method is also disclosed to make such fusion proteins at good expression levels. These recombinant hFSH-Fc fusion proteins of the present disclosure exhibit sufficient biological activities and prolonged plasma half-lives, leading to improved pharmacokinetics and pharmacodynamics. Thus, a lower dosage may be used and/or better or different therapeutic efficacies with less side effects may be achieved. A method for the application of the recombinant hFSH-Fc fusion proteins in the treatment and/or prevention of human infertility is also disclosed.

13 Claims, 5 Drawing Sheets

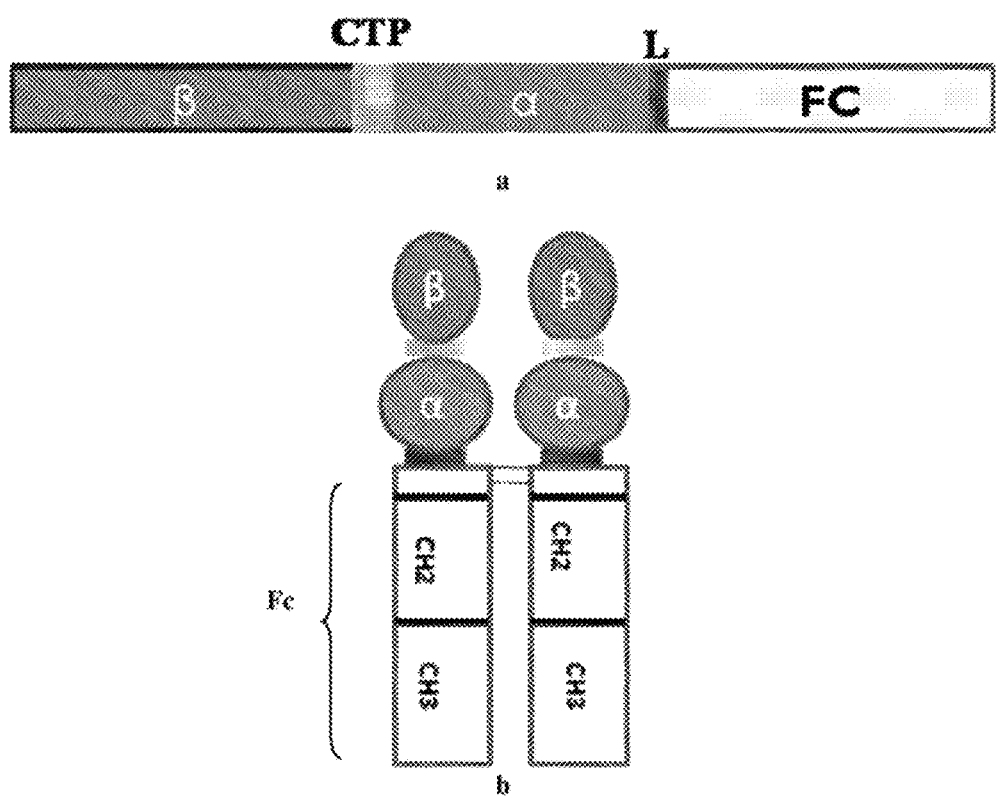

SEQUENCE ID NO: 2

```
  1 M K T L Q F F F L F C C W K A I C C W S
  1 ATGAAGACCCTGCAGTTCTTTTTCCTGTTTTGCTGTTGGAAGGCAATCTGCTGTAACTCA
 21 C E L T N I T I A I E K E E C R F C I S
 61 TGTGAGCTGACTAATATCACCATTGCCATCGAAAAAGAGGAATGCAGGTTCTGTATTAGT
 41 I N T T W C A G Y C V T R D L V Y R D P
121 ATCAACACTACCTGGTGCGCTGGCTACTGTTATACAAGGGATCTGGTGTATAAGGACCCA
 61 A R P K I Q K T C T F K E L V Y E T V R
181 GCACGGCCCAAAATCCAGAAGACATGCACTTTCAAGAACTGGTGTACGAGACTGTGAGG
 81 V P G C A H H A D S L Y T Y P V A T Q C
241 GTCCCTGGCTGTGCCCACCATGCTGATTCCCTGTACACTTATCCAGTGGCCACCCAGTGC
101 R C G K C D S D S T D C T V R G L C P S
301 CACTGTGGAAAGTGCGATAGTGACTCAACAGACTGTACTGTGCGAGGCCTGGGACCTTCT
121 Y C S F G E M K E P R F Q D S S S K A
361 TACTGCAGTTTTGGCGAAATGAAGGAGCCCCGTTTCCAGGATTCCAGCTCTAGTAAAGCT
141 P P S L P S P S R L P G P S D T P I L
421 CCCCCTCCTTCCCTGCCCTCACCCTCAAGACTGCCTGGACCTTCCGACACTCCCATCCTG
161 P Q A P D V Q D C P E C T L Q E M P F F
481 CCACAGGCCCCCGATGTGCAGGACTGCCCTGAATGTACTCTGCAGGAGAACCCCTTCTTT
181 S Q P G A P I L Q C M G C C F S R A Y P
541 TCTCAGCCCGGCGCTCCTATCCTGCAGTGTATGGGATGCTGTTTTAGTAGAGCATATCCT
201 T P L R S K K T M L V Q K N V T S E S T
601 ACCCCACTGCGCTCAAAGAAAACAATGCTGGTCCAGAAGAATGTGACAAGCGAATCTACT
221 C C V A K S Y N R V T V M G G F K V E N
661 TGCTGTGTGGCTAAATCCTACAACCGCGTGACCGTGATGGGCGGCTTCAAGGTGGAGAAT
241 H T A C H C S T C Y Y H K S G S G G S
721 CACACAGCATGCCATTGTTCTACTTGCTACTACCATAAGAGTGGATCCGGTGGCGGTTCC
261 G G G S G G G S V E C P P C P A P P
781 GGTGGAGGCGGAAGCGGCGGTGGAGGATCAGTGGAGTGCCCTCCATGTCCAGCACCCCCT
281 V A G P S V F L F P P K P K D T L M I S
841 GTCGCAGGTCCATCTGTGTTCCTGTTTCCACCCAAGCCTAAAGACACTCTGATGATCTCC
301 R T P E V T C V V V D V S H E D P E V Q
901 CGCACCCCAGAAGTCACCTGTGTGGTCGTGGATGTGAGCCATGAAGACCCCGAGGTCCAG
321 F N W Y V D G V E V H N A K T K P R E E
961 TTCAATTGGTACGTGGATGGCGTCGAGGTGCACAACGCTAAGACAAAACCTAGAGAAGAG
341 Q F N S T F R V V S V L T V V H Q D W L
1021 CAGTTCAACTCTACCTTTCGCGTCGTGAGTGTGCTGACAGTCGTGCACCAGGACTGGCTG
361 N G K E Y K C K V S N K G L P A S I E K
1081 AATGGCAAGGAGTATAAGTGCAAAGTGAGCAACAAAGGACTGCCTGCCTCAATCGAAAAG
381 T I S K T K G Q P R E P Q V Y T L P P S
1141 ACTATTTCCAAGACCAAAGGACAGCCAAGAGAGCCCCAGGTGTACACCCTGCCTCCAAGC
401 R E E M T K N Q V S L T C L V K G F Y P
1201 CGCGAAGAGATGACTAAAAATCAGGTCTCTCTGACCTGTCTGGTGAAGGGGTTTTATCCT
421 S D I A V E W E S N G Q P E N N Y K T T
1261 AGTGATATCGCCGTGGAATGGGAGTCAAACGGTCAGCCAGAGAACAATTACAAGACCACA
441 P P M L D S D G S F F L Y S K L T V D K
1321 CCCCCTATGCTGGACAGCGATGGGTCTTTCTTTCTGTATAGCAAACTGACAGTGGACAAG
461 S R W Q Q G N V F S C S V M H E A L H N
1381 TCTCGGTGGCAGCAGGGTAACGTCTTCTCTTGCAGTGTGATGCACGAAGCACTGCACAAT
481 H Y T Q K S L S L S P G K *
1441 CATTACACCCAGAAGTCACTGTCACTGAGCCCAGGAAAATGA
```

Figure 3

LONG-ACTING RECOMBINANT HUMAN FOLLICLE-STIMULATING HORMONE-FC FUSION PROTEIN

TECHNICAL FIELD

The present disclosure relates to molecular biology and medicine. More specifically, the present disclosure relates to a long-acting recombinant fusion protein of human follicle-stimulating hormone, the preparation method and the use thereof. The fusion protein has significantly extended the half-life in vivo, and has better therapeutic efficacy than that of the existing human follicle-stimulating hormone.

BACKGROUND

Infertility affects one in seven couples worldwide, becoming a severe disease right after cancer and cardiovascular disease in terms of its harmful effect on human health. Follicle-stimulating hormone (FSH), either extracted from urine or produced by genetic engineering, has been widely used by specialists to improve fertility.

The use of human FSH (hFSH) extracted from human urine is limited by its high cost, labor-intensive collection and the difficulty in tracing urine sources as well as the potential risk of virus contamination. The recombinant hFSH is a better option as it can avoid the above problems. hFSH is a glycoprotein with a molecular weight of about 43 kilodalton (kD). As a therapeutic drug, it is necessary to maintain the correct 3-dimensional structure and glycosylation to maintain its bioactivity. The ability to perform complex post-translational modifications is a major reason that most therapeutic biologicals are produced in mammalian cell lines. Among them, the Chinese Hamster Ovary (CHO) cell system is the most common host cell system for eukaryotic gene expression. Therapeutic recombinant proteins such as EPO and G-CSF have been successfully expressed in CHO cells. These proteins can not only be folded and glycosylated properly, but also be secreted in favor of the subsequent downstream processes, such as purification.

Although the recombinant hFSH produced by CHO cells has been in the market for years, several defects still need to be solved. First, the current recombinant FSH has a short plasma half-life, thus requiring patients being administered repeatedly to achieve optimal therapeutic efficacy. For example, hFSH must be administered intramuscularly or subcutaneously as daily injection routinely for 8-12 days or more when used for ovulation induction, resulting in poor compliance. In addition, this treatment regimen is often accompanied with severe cytotoxic effects to nervous, endocrine and immune system, causing a number of frequently-occurring complications such as ovarian hyperstimulation syndrome, clinical manifestations associated with ovarian enlargement, increased vascular permeability and the formation of ascites, which can be life-threatening in severe cases. Furthermore, the production cost of the recombinant hFSH is very high due to the low level of cell expression and the intensive production process. Last but not least, hFSH is a glycosylated protein comprising an α-subunit and a β-subunit linked via non-covalent bond, and its bioactivity depends on the correct assembly of the two subunits. It remains challenging to maintain the right assembly of the two subunits during the expression and purification process of protein in order to obtain a biologically active molecule useful for therapeutic purpose until the present disclosure. To overcome the defects and insufficiency of the existing hFSH products, the present disclosure provides a new molecule of recombinant hFSH with prolonged plasma half-life, sufficient biological activity and high level of protein expression, resulting in improved pharmacokinetics and/or pharmacodynamics. Thus, a lower dosage may be used and/or better or different therapeutic efficacy with less side effects may be achieved.

SUMMARY

The present disclosure relates to a human follicle-stimulating hormone-Fc fusion protein (hereinafter to be also referred to as hFSH-Fc). The present disclosure also provides methods for the preparation of the fusion protein and its use or application, aiming at overcoming the defects of the current FSH, such as the low expression level, the intensive purification process and the short plasma half-life.

One embodiment of the present disclosure relates to an hFSH-Fc fusion protein. This fusion protein comprises hFSH β, CTP, hFSH α, a flexible peptide linker (hereinafter to be also referred to as L), and human IgG2 Fc variant (vIgG2Fc), as shown in SEQ ID NO:2 (hFSH β-CTP-hFSH α-L-vIgG2Fc amino acid sequence), wherein hFSH β is a beta subunit of FSH, hFSH α is an alpha subunit of FSH, L is a flexible peptide linker. The fusion protein of the present disclosure is abbreviated as hFSH-Fc.

Another embodiment of the present disclosure is that the 1-18 amino acid residues of the regular hFSH β-subunit are deleted from the amino acid sequence of said hFSH β subunit, as shown in SEQ ID NO:5.

Another embodiment of the present disclosure is that the 1-24 amino acid residues of the regular hFSH α-subunit are deleted from the amino acid sequence of said hFSH α-subunit, as shown in SEQ ID NO:3.

Another embodiment of the present disclosure is that the sequence of the CTP (carboxy-terminal peptide) refers to the 28-34 amino acid residues of C-terminal of HCG β subunit, preferably, CTP is the 33 amino acid residues from the C-terminal of HCG β subunit, as shown in SEQ ID NO:4.

Another embodiment of the present disclosure provides a flexible peptide linker comprising about 20 or fewer amino acids, more preferably from about 2 to 20 amino acids in length and the flexible peptide linker contains or comprises two or more amino acids selected from the group consisting of glycine, serine, alanine and threonine, preferably, the amino acid sequence of a flexible peptide linker is GlySerGlyGlyGlySerGlyGlyGlyGlySerGlyGlyGlyGlySer (as shown in SEQ ID NO:6).

Another embodiment of the present disclosure provides the human IgG2 Fc variant of the present disclosure which comprises a hinge, CH2 and CH3 domains of human IgG2 with Pro331 Ser mutant.

The following chapters are detailed descriptions of IgG Fc variant, peptide linker and CTP.

IgG Fc Variant

Human immunoglobulins are the most abundant proteins in the blood, their plasma half-life can be up to 21 days. The main reason is that every immunoglobulin comprises an Fc fragment, which has a unique function to stabilize the protein.

The Fc region of human immunoglobulins plays a significant role in immune defense system for the elimination of pathogens. Effects or functions of IgG are mediated via the Fc region by two major mechanisms: (1) binding to Fc receptors (Fcγ Rs) on the cell surface, thus leading to the ingestion of pathogens by phagocytosis or lysis by killer cells via the antibody-dependent cellular cytotoxicity (ADCC) pathway, or (2) binding to the C1q part of the first complement component C1, initiating the complement-dependent cytotoxicity (CDC) pathway, thereby resulting in the lysis of pathogens. Among the four human IgG isotypes (IgG1, IgG2, IgG3, IgG4), almost no human IgG2 binds to Fcγ R. In addition, the affinity of human IgG2 appears to be quite weak when binding to C1q and activating the complement cascade. For the therapeutic use, when hFSH-Fc binds to various target cells, it is determinative or important that the Fc region of the fusion protein should not mediate effects or functions, thereby not leading to the lysis or removal of the target cells. Accordingly, it will become evident from the present disclosure that the Fc region of hFSH-Fc should be Fc variant with non-lytic nature. As discussed above, natural IgG Fc mediates various levels of effects or functions. In contrast, Fc with non-lytic nature is inert in terms of binding to Fcγ Rs and C1q to trigger the effects or functions. To obtain a non-lytic Fc, certain amino acids of the natural Fc region have to be mutated in order to attenuate the function of the effector.

By comparing the amino acid sequences of human IgG isotypes, a portion of Fc near the N-terminal of the CH2 domain is found to play an important role in the binding of IgG Fc to Fcγ Rs, and a portion of Fc near the C-terminal of the CH2 domain is critical in the binding of IgG to C1q. IgG2 does not bind to Fcγ Rs, and binds to C1q weakly. To minimize the CDC activity mediated by the binding of Fc to C1q, IgG2 has been altered in this motif with Pro331Ser mutation (as shown in FIG. 1). The Fc variant shows the minimized function of the effector compared to natural IgG2Fc, which is more suitable for the production of the recombinant hFSH-Fc fusion protein.

Peptide Linker

The length of the peptide linker plays an important role in the bioactivity of the recombinant dimeric protein. It has been reported that homodimeric EPO with two complete EPO subunits separated by a peptide linker of 3-7 amino acids shows decreased bioactivity compared to the normal EPO (see, for example, Qiu H et al. J Biol Chem, 273: 11173-11176, 1998). However, when the length of the peptide linker between the two EPO molecules reaches 17 amino acids, the in vitro and in vivo bioactivity of the homodimeric EPO increases significantly (see, for example, Sytkowski A J et al. J Biol Chem, 274:24773-24778, 1999; U.S. Pat. No. 6,187,564). A possible explanation is that as the increase of the length of the peptide linker between the functional molecules, steric hindrance decreases, the two functional molecules will not interfere with each other any more (see, for example, Ashkenazi A et al. Curr Opin in Immunol, 9:195-200, 1997).

The present disclosure for the first time provides a unique peptide linker in the hinge region to minimize the steric hindrance, a method to produce homodimeric hFSH-Fc fusion protein with the C-terminal of hFSH α binding to the Fc mutant via a soft peptide linker. Instead of diminishing the bioactivity of FSH, this homodimeric hFSH-Fc fusion protein can maintain or even improve the bioactivity of FSH. The sequence of amino acid residues of the preferable peptide linker is: GlySerGlyGlyGlySerGlyGlyGlyGlySerGlyGlyGlyGlySer, (as shown in SEQ ID NO:6).

CTP

Glycosylation is very important for the bioactivity and the plasma half-life of proteins. There are two types of glycosylation sites on a glycosylated protein, one is N-glycosylation site and the other is O-glycosylation site. CTP is a 28-34 amino acid-long peptide derived from the C-terminal of HCG β-subunit, and it has been reported that HCG has a much longer plasma half-life than hFSH, mainly due to the glycosylation of CTP. The CTP possesses sites of O-glycosylation, which will increase the glycosylation level of the protein, thus leading to improved pharmacokinetics and pharmacodynamics, such as the increase of bioactivity and the in vivo half-life.

The present disclosure provides a recombinant hFSH-Fc fusion protein with the following characteristics. The hFSH-Fc fusion protein is a homodimeric protein which comprises β-subunit of hFSH (hFSH β), CTP, α-subunit of hFSH (hFSH α), a flexible peptide linker, and human IgG2 Fc variant (vIgG2Fc). The human IgG2 Fc variant can prolong the in vivo half-life of fusion protein and stabilize the protein. Fc variant with non-lytic feature can reduce the function of the effector to the maximum extent caused by its binding with Fc γ Rs and C1q, suppress the ADCC and CDC pathway effectively, thus causing reduced cell cytotoxicity. CTP can increase the bioactivity and prolong the in vivo half-life of the protein without immunogenicity. CTP serves as a bridge between the α-subunit and the β-subunit of hFSH, leading to the decrease of the steric hindrance and contributing to the protein assembly and function. A soft peptide linker is inserted between the C-terminal of hFSH α and an Fc variant, thereby maintaining or even increasing the bioactivity of the hFSH-Fc fusion protein.

For the first time until the present disclosure, the CTP, peptide linker and IgG2 Fc variant are linked together in sequence with an hFSH molecule, producing an innovative recombinant hFSH fusion protein. The elaborately designed arrangement of CTP, peptide linker and IgG2 Fc variant can prolong the plasma half-life significantly without affecting the spatial configuration and the bioactivity of hFSH, leading to minimized injection times and side effects.

In another embodiment of the present disclosure, a method of preparing or producing such recombinant hFSH-Fc fusion protein from a mammalian cell line such as a CHO-derived cell line is disclosed. A method of preparing the recombinant fusion protein includes the following procedures.

(1) Construct an expression vector containing DNA encoding the hFSH-Fc fusion protein;
(2) Generate stable mammalian cell lines expressing the fusion protein;
(3) Culture cells to high density;
(4) Purify the recombinant hFSH-Fc fusion protein.

According to the present disclosure, a method of constructing expression vector containing DNA encoding the hFSH-Fc fusion protein is disclosed. The codon of nucleotide sequence of the hFSH-Fc gene is optimized and then synthesized (as shown in SEQ ID NO: 1). The fusion gene sequence is then inserted into a mammalian cell expression vector, resulting in the plasmid pCDNA3-hFSH-Fc containing hFSH-Fc gene (FIG. 4). Nucleotide sequence optimization is based on codon preference of the mammalian host cells.

The expression vector of mammalian cells may be commercially available but not limited to the vectors suitable for eukaryotic expression such as pCDNA3, pCMV/ZEO, pIRES, pDR, pBK, pSPORT etc., preferably pCDNA3.

For the present disclosure, a method of generating stable mammalian cell lines expressing the recombinant hFSH-Fc fusion protein is disclosed. The expression plasmid containing hFSH-Fc gene is transfected into suitable mammalian host cells, and the cell lines are then screened for those highly expressing the target protein stably.

The mammalian host cells include CHO, HEK293, COS, BHK, NSO and Sp2/0, preferably CHO, more preferably dihydrofolate reductase (DHFR) deficient CHO cell, which has been adapted to the suspension culture in serum free medium (CHO DHFR−).

The transfection methods include phosphate calcium method, electroporation method and liposome transfection method, preferably electroporation method.

A method of screening and obtaining cell lines of stable producers of FSH-Fc fusion protein is disclosed. Cells expressing fusion protein are initially screened by the screening markers, and the stable cell lines of high producers are made by amplificable selectable markers. Screening markers are known in the art to be any suitable selective resistance markers, for example, ZEO (Zeocin), G418 (amino glycosides antibiotics), PUR (puromycin) or HYP (Hygromycin), preferably ZEO. A screening marker is also well known in the art to be any fluorescent labeling gene, including GFP (green fluorescent protein), RFP (red fluorescent protein), preferably GFP. Amplificable selectable markers are known in the art to be DHFR (DHFR) sequence or GS (Glutamine synthetase) sequence, preferably DHFR. Due to the cells of CHO-DHFR− are lack of dihydrofolate reductase, they can not synthesize tetrahydrofolate on their own, in order to survive, the addition of hypoxanthine, thymidine and glycine in the culture medium becomes essential. However, when the target gene is co-transfected with the DHFR gene, not only those cells can grow in the culture medium without the additives mentioned above, but also MTX resistant cell lines can be obtained since DHFR can be inhibited by MTX (methotrexate, folic acid analogue). Under the selection pressure of MTX, DHFR gene must amplify to a certain large copy number in order to survive, and as the target gene together with the co-transfected DHFR gene are prone to integrate into the same domain of the cell chromosome, they are amplified simultaneously, leading to the expression of large amount of exogenous target protein.

Also according to this disclosure, a method of high-density cell culture is disclosed to produce the recombinant hFSH-Fc fusion protein. The above-mentioned stable cell line is transferred to a shaking flask or bioreactor to culture in a larger scale, especially by optimizing the culture condition, the present disclosure achieves high level expression of the recombinant hFSH-Fc fusion protein in the culture medium. The method can realize a high density cultivation of cells, increase the quality and the yield of the recombinant protein, and also improve the degree of glycosylation and the content of sialic acid.

The optimized condition of cell culture includes the cooling culture method, specifically, when the cell density reaches $1\times10^7$/mL, the culture temperature is reduced from 37° C. to 33° C., then the cells are cultured at 33° C. until the cumulative protein production level stops increasing. This method can increase the bioactivity and the cumulative yield of the target protein.

The optimized condition of cell culture also includes the supplement of special additives in the culture medium, preferably, adding 100 μM $Cu^{2+}$ to the basic medium and 2 mm ManNAc (N-acetyl-D-amino mannose) to the feeding medium. This method of adding additive supplement can increase the degree of glycosylation and the content of sialic acid by 20%.

For the present disclosure, a method for purifying the recombinant hFSH-Fc fusion protein is disclosed as the following procedures.

1) Protein A affinity chromatography: centrifuge the culture medium and collect the supernatant, use Protein A affinity chromatography to capture the target hFSH-Fc fusion protein based on the characteristics of the fusion protein coupled to an Fc fragment.

2) Hydrophobic chromatography: Based on the hydrophobic characteristic of the recombinant hFSH-Fc fusion protein, use hydrophobic chromatography to further remove the impurities from the eluent of Protein A chromatography. The suitable resins for hydrophobic chromatography can be selected from the following options: Butyl Sepharose 4 Fast Flow, Octyl Sepharose 4 Fast Flow, Phenyl Sepharose 6 Fast Flow, Butyl-S Sepharose 6 Fast Flow, Butyl Sepharose 4B, Octyl Sepharose CL-4B and Phenyl Sepharose CL-4B, preferably Phenyl Sepharose 6 Fast Flow.

The present disclosure discloses a preparation method of the recombinant hFSH-Fc fusion protein with high expression yield, and due to its coupling to an IgG2 Fc variant, a convenient and efficient purification process can be achieved by the protein A affinity chromatography. The purity of the fusion protein reaches 98% or more after the subsequent hydrophobic chromatography. In addition, the α and β chain of the recombinant hFSH-Fc fusion protein of the present disclosure can be correctly folded together, avoiding the formation of α-α dimer and β-β dimer, simplifying the purification process greatly and reducing the production cost significantly.

Another embodiment of the present disclosure provides a pharmaceutical composition comprising the recombinant hFSH-Fc fusion protein, wherein the pharmaceutical composition comprises a pharmaceutically acceptable carrier, excipient or diluent, and an effective amount of the recombinant hFSH-Fc fusion protein of the present disclosure.

Specifically, the pharmaceutical composition contains an effective dose (such as 0.000001-90 wt %, preferably 0.1-50 wt %, more preferably 5-40 wt %) of the recombinant hFSH-Fc fusion protein and a pharmaceutically acceptable carrier. Typically, an effective amount of the fusion protein is formulated into a non-toxic, inert and pharmaceutically acceptable aqueous carrier, the pH of the formulation is usually about 5-8, preferably 6-8.

According to this disclosure, the pharmaceutical acceptable carrier includes but are not limited to sucrose, mannitol, Tween 20, methionine, saline, buffer, glucose, water, glycerol, and the composition thereof. Typically, the pharmaceutical preparation of the compositions and the administration route should be matched, wherein the pharmaceutical preparation of the composition in the present disclosure can be formulated into injection by conventional methods using saline or a solution containing glucose and other excipients. The pharmaceutical composition is manufactured under sterile condition. The amount of active ingredients is the effective therapeutic dose. The pharmaceutical preparation of the present disclosure can be also formulated into a sustained-release form.

The effective amount of the fusion protein of the present disclosure can be varied according to the mode of administration and the severity of the disease. The preferred effective amount of the fusion protein can be determined by those skilled in the art based on a variety of factors such as clinical trials. The factors include but are not limited to the pharmacokinetic parameters of the fusion protein such as bioavailability, metabolic rate and half-life, the severity of disease, patient's weight, patient's immune status and the administration route etc.

A further embodiment of the present disclosure provides a method for the application of the recombinant hFSH-Fc fusion protein in the treatment and/or the prevention of human infertility.

The recombinant hFSH-Fc fusion protein of the present disclosure prolongs the in vivo half-life significantly, leading to improved pharmacokinetics and pharmacodynamics, thereby reducing not only the number of injections and the side effects, but also the pain and economic burden of patients compared with the existing hFSH in clinical application.

There are many advantages of the present disclosure stated below in terms of the recombinant hFSH-Fc fusion protein and the preparation method.

1) The recombinant hFSH-Fc fusion protein is a novel fusion protein comprising the CTP, a peptide linker, human IgG2 Fc variants (vIgG2Fc) and hFSH linked in right sequence. The hFSH-Fc fusion protein maintains the correct spatial configuration of hFSH, significantly prolongs the in vivo half-life and greatly improves the expression level in CHO cells. Moreover, the in vitro and in vivo bioactivity of the recombinant hFSH-Fc fusion protein is similar to those of the existing hFSH.

2) The α and β chain of the homodimeric hFSH-Fc fusion protein is coupled correctly by covalent bonds, avoiding the formation of α-α dimer and β-β dimers, greatly simplifying the purification process and reducing the production cost.

3) The in vivo half-life of the recombinant hFSH-Fc fusion protein is prolonged significantly, and its plasma half-life is four times longer than the existing hFSH, leading to the significant reduction of the injection times and the side effects caused by the existing treatment regimens in clinical application.

BRIEF DESCRIPTIONS OF THE DRAWINGS

FIG. 1 shows the comparison of the amino acid sequence of the hinge and CH2 region of human IgG2 and its variants. Three portions are compared: amino acid position 228, 234-237, and 330-331. Amino acid mutations of the variants are indicated in bold italics. The EU numbering system is used for the amino acid residues.

FIG. 2 shows the schematic diagram of the single stranded and dimerized recombinant hFSH-Fc protein. a) single stranded hFSH-Fc; b) dimerized hFSH-Fc.

FIG. 3 shows the nucleotide sequence and deduced amino acid sequence of the hFSH-Fc fragment between HindIII and EcoRI fragment in pCDNA3 expression vector. The nucleotide sequence of the recombinant hFSH-Fc comprises a leading peptide (amino acid residues 1-18), hFSH β chain, CTP, mature hFSH α chain, peptide linker, and IgG2Fc variant (vIgG2Fc). Mature recombinant hFSH-Fc fusion protein contains mature hFSH β chain (amino acid residues 19-129), CTP (amino acid residues 130-162), mature a chain (amino acid residues 163-254), peptide linker (amino acid residues 255-270) and IgG2Fc variant (vIgG2Fc) (amino acid residues 271-493).

FIG. 4 shows the schematic representation of eukaryotic expression plasmid pCDNA3-hFSH-Fc. The full length of the plasmid is 9063 bp, comprising 10 major gene fragments, i.e., (1) CMV promoter, (2) target gene hFSH-Fc, (3) IRES, (4) the zeocin resistance gene, (5) BGH terminator, (6) SV40 promoter, (7) DHFR amplification gene, (8) SV40 terminator, (9) Ampicillin resistance gene (ampicillin), (10) the ColE1 origin of replication (Ori).

DETAILED DESCRIPTION

The present disclosure will be further elaborated with the illustrative embodiments below. The methods are intended to illustrate but not intended to limit this disclosure. Specific experimental condition which is not stated in the following embodiments can be operated according to the conventional condition as described in Sambrook etc. Molecular cloning: a laboratory manual (New York: Cold Spring Harbor Laboratory Press press, 1989), or the manufacturer's recommendation.

Example 1. Preparation of the Gene Encoding Recombinant hFSH-Fc Fusion Protein

The design of the gene sequence was optimized on the basis of the preferred codons of CHO cells. The gene encoding leader peptide and mature protein of hFSH β chain, CTP and the mature protein of hFSH α chain were synthesized de novo. The resulting DNA fragment of 756 bp in length was inserted into a holding vector such as pUC57 at the EcoRV restriction enzyme site to provide the phFSH plasmid. The sequence of the hFSH gene was confirmed by DNA sequencing.

The gene encoding linker peptide (L) and human IgG2Fc variant (vIgG2Fc) with restriction sites of BamHI (5') and EcoRI (3') was synthesized de novo. Resulting DNA fragment of L-vIgG2Fc was inserted into a holding vector such as pUC19 between the BamHI and EcoRI sites to provide the pL-vIgG2Fc plasmid. The sequence of the pL-vIgG2Fc gene was confirmed by DNA sequencing. To prepare the hFSH-L-Fc fusion gene, the hFSH fragment containing the leader peptide sequence, hFSH β, CTP and hFSH α was excised from the phFSH plasmid with SpeI and BamHI, and then purified by agarose gel electrophoresis. The purified fragment was then inserted to the 5'-end of the peptide linker in the pL-vIgG2Fc plasmid, linked by T4 ligase to provide the phFSH-L-vIgG2Fc plasmid. The resulting fusion gene of phFSH-L-vIgG2Fc plasmid comprised hFSH β, CTP, hFSH α, peptide linker, and Fc variant gene. The single stranded structure is shown in FIG. 2a and the dimeric structure is shown in FIG. 2b.

Figure 4:
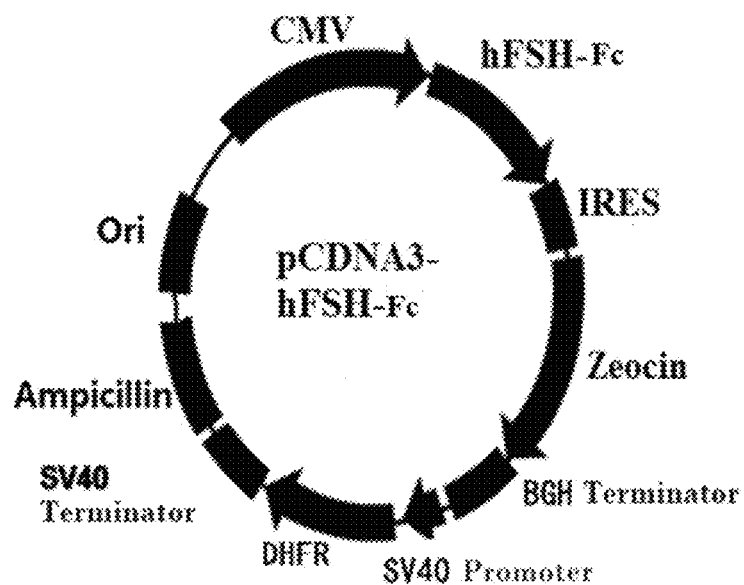

To construct the expression vector for hFSH-Fc, the hFSH-L-vIgG2Fc fragment was excised from the phFSH-L-vIgG2Fc plasmid with restriction enzyme SpeI and EcoRI and was purified by agarose gel electrophoresis. The purified fragment was then inserted into the corresponding restriction sites of the mammalian expression plasmid such as pcDNA3 (Invitrogen) to provide the pCDNA3-hFSH-L-vIgG2Fc plasmid (pCDNA3-hFSH-Fc), as shown in FIG. 4. The plasmid comprised a cytomegalovirus (CMV) early gene promoter-enhancer which was required for high level expression of exogenous protein and two kinds of selective marker gene, leading to ampicillin resistance in bacteria and zeocin resistance in mammalian cells. In addition, this expression vector comprised the dihydrofolate reductase (DHFR) gene which was in a position to enable the co-amplification of the hFSH-L-vIgG2Fc fusion gene together with the DHFR gene in the presence of methotrexate (MTX) when the host cells were deficient in DHFR gene expression.

Linking the α chain and β chain of hFSH by CTP fragment can be favorable for the right assembly of the α chain and β chain. The presence of a peptide linker, preferably a flexible linker between the hFSH and Fc moieties (and chemically bound to both moieties), increases the flexibility of the hFSH domain and enhances its biological activity. For the present disclosure, a peptide linker of about 20 or fewer amino acids in length is preferred. While single amino acid is within the scope of the present disclosure, it is preferred to have a flexible peptide linker of about 20 to about 2 amino acids in length. Peptide linker containing or comprising two or more amino acids selected from the group consisting of glycine, serine, alanine and threonine can be used preferably. One embodiment of the present disclosure has the peptide linker containing a Gly-Ser peptide component, and its amino acid sequence is GlySerGlyGlyGlySerGlyGlyGlyGlySerGlyGlyGlyGlySer, as shown in SEQ ID NO:6.

Example 2. Stable Expression of the Recombinant hFSH-Fc Fusion Protein in Mammalian Cells The pCDNA3-hFSH-L-vIgG2Fc expression vector plasmid constructed from example 1 was transfected into a mammalian host cell line to achieve the expression of the fusion protein. For stable high level of expression, a preferred host cell line was CHO cells deficient in DHFR enzyme (CHO DHFR−). FIG. 2b shows the schematic diagram of the recombinant dimerized hFSH-Fc fusion protein. A preferred method of transfection was electroporation. 10 μg of plasmid DNA linearized with PvuI was added to 2 to 5×10$^7$ cells in a cuvette by using Gene Pulser Electroporator (Bio-Rad Laboratories, Hercules, Calif.) set at an electric field of 250 V and a capacitance of 960 μFd. Two days following the transfection, the media was replaced with growth media containing 100 μg/mL Zeocin resistance-marker gene. Transfectants resistant to the chemical used for selection were analyzed for the expression level of the hFSH-Fc protein by Western blotting using anti-hFSH antibody. To achieve higher level of the fusion protein expression, co-amplification was carried out by utilizing the gene of DHFR that could be inhibited by MTX. In growth media containing increasing concentration of MTX, the transfected fusion protein gene was co-amplified with the DHFR gene. Transfectants capable of growing in the media with up to 10 μM/mL of MTX were then subcloned by limiting dilution method. The subcloned cells were further analyzed by measuring the secretion rates. To obtain stable cell lines with high expression of the recombinant hFSH-Fc fusion protein, cell clones yielding secretion rate level over 10 μg/million cells/24 h (preferably about 20 μg/million cells/24 h) were adapted to the suspension culture using serum-free growth media.

Example 3. Purification and Characterization of the Fusion Protein

Figure 5:
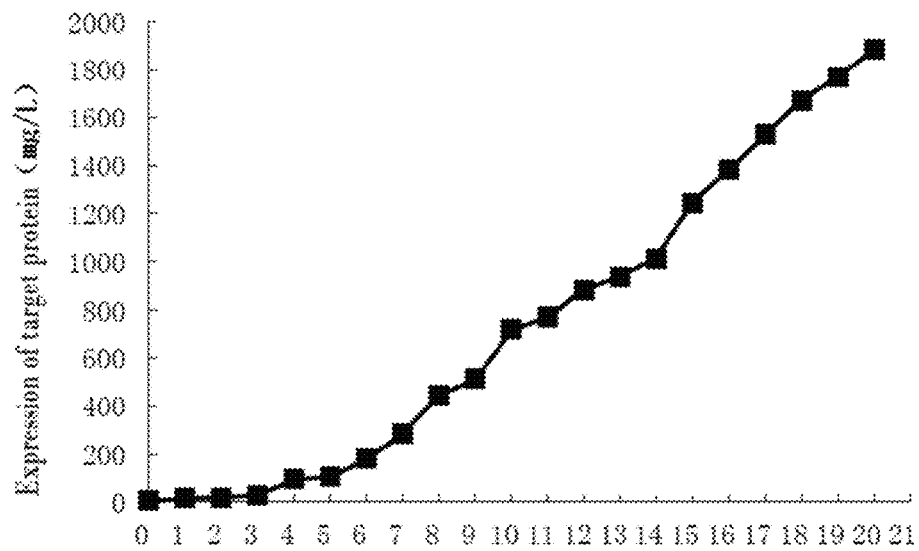
FIG. 5 shows the cumulative recombinant hFSH-Fc protein level (mg/L) secreted from the cells cultured in a 7 L bioreactor.

The high expression cell line from Example 2 first underwent a domestication process using serum-free medium in the culture dish, and was then transferred to the shake flask for suspension culture. During the above culture process in serum-free medium, medium optimization was also carried out to test different ingredients to detect various parameters, such as the growth state, growth trend, bioactivity and sialic acid etc. The following condition of cell culture was preferred: basic medium comprising 100 μM Cu$^{2+}$, feeding medium comprising 2 mM ManNAc (N-acetyl amino mannose). This culture condition can increase the glycosylation extent of the recombinant hFSH-Fc fusion protein and cause about 20% increase of the content of sialic acid. For cell growth in a 7 L bioreactor, when the cell density reached 1×10$^7$/mL at 37° C., the culture temperature was adjusted to 33° C. to allow longer accumulation and the secreted fusion protein was more stable than those at 37° C. The optimum culture period for one batch of cell production was approximately 20 days. Small amount of the recombinant fusion protein was initially purified by chromatography using 1 mL Protein A column to determine the expression level, as shown in FIG. 5, the cumulative yield of the recombinant hFSH-L-vIgG2Fc cell line was 1.87 g/L.

The Purification of the Recombinant hFSH-Fc Fusion Protein Included the Following Steps:

1) Protein A affinity chromatography: The culture media containing the hFSH-Fc fusion protein was centrifugated, and the supernatant was collected for subsequent loading onto a Protein A column pre-equilibrated with phosphate-buffered saline (PBS). After the binding of the fusion protein to the Protein A resin, the flow-through fractions were discarded. The column was then washed with PBS until the OD at 280 nm was below 0.01. The bound fusion protein was eluted with 20 mM sodium acetate buffer (pH 4.0), and the elution was neutralized with 1M Tris-HCl buffer (pH10.0). The purity of the hFSH-Fc protein could reach 95% or more after this step.

2) Hydrophobic chromatography: The elution from the above Protein A chromatography was changed to 20 mM Tris-HCl-1.5 M NaCl (pH8.0) buffer with ultrafiltration method, and loaded onto a phenyl-6 Fast Flow column equilibrated with 20 mM Tris-HCl-1.5 M NaCl (pH8.0) buffer. The column was washed with the same equilibration buffer, and then washed with 20 mM Tris-HCl-1.35M NaCl (pH8.0) buffer before its elution with 20 mM Tris-HCl-0.5M NaCl (pH8.0) buffer.

Figure 6:
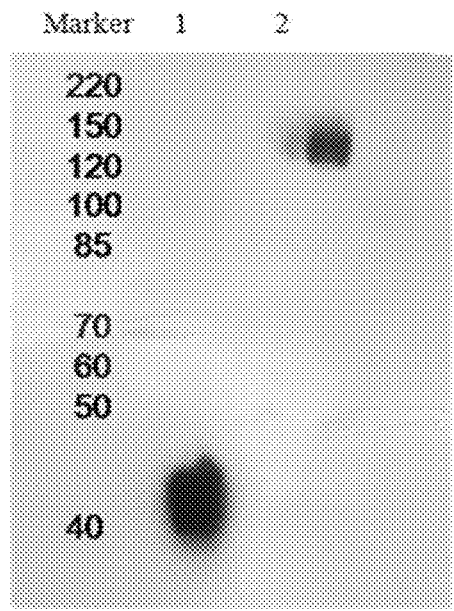
FIG. 6 shows successful expression of the recombinant hFSH-Fc fusion protein in CHO cells by Western blotting analysis in non-reduced SDS-PAGE: Lane 1, human urinary hFSH (about 43 kDa); Lane 2, the recombinant hFSH-Fc fusion protein of the present disclosure (about 140 kDa).
Figure 7:
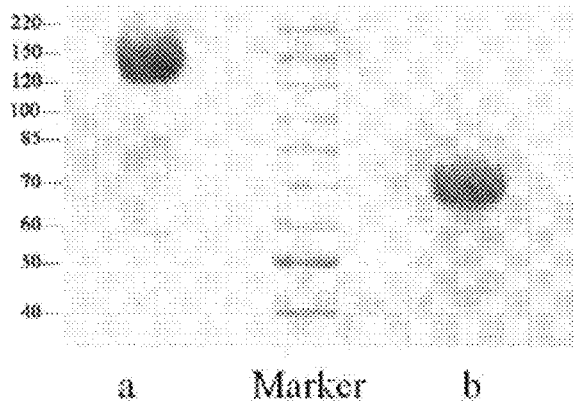
FIG. 7 shows the map of 10% SDS-PAGE of the single stranded and dimerized hFSH-Fc under reduced condition and non-reduced condition. a) non-reduced, dimerized hFSH-Fc (about 140 kDa); b) reduced, single stranded hFSH-Fc (about 70 kDa).

As shown in FIG. 6, Western blotting analysis indicated that the recombinant hFSH-Fc fusion protein in CHO cells was successfully expressed. Non-reduced SDS-PAGE showed the hybridization bands of the target protein respectively: (1) 43 kDa band, human urine hFSH (commercial product); (2) 140 kDa band, the recombinant hFSH-Fc fusion protein (the present disclosure), proving that the recombinant hFSH-Fc fusion protein comprised the hFSH component. FIG. 7 indicated the SDS-PAGE of the hFSH-Fc fusion protein under reduced and non-reduced conditions. The results demonstrated that the purity of the hFSH-Fc protein could reach 98% or more, and the molecular weight of the hFSH-Fc protein under reduced condition was half of that under non-reduced condition.

Example 4. In Vitro and In Vivo Bioactivity Assay

The in vitro bioactivity of the recombinant hFSH-Fc fusion protein (immunological activity) was assayed by ELISA kit from BIOCHECK (USA) Company. Experimental procedure was conducted according to the specification of the kit. The in vivo activity was assayed by measuring the ovarian weight gain based on the 2010 edition of the British Pharmacopoeia. Protein quantitation was determined using the traditional LOWRY method. According to the British Pharmacopoeia, small amount of background HCG (70

IU/ml) was used to increase the assay sensitivity for ovarian weight gain in rats. Sample diluent comprising 70 IU/ml HCG was prepared by adding 0.1% albumin phosphate buffer (pH7.2±0.2). For the in vivo assay, each sample diluent (pH7.2±0.2) was prepared to equally contain 1.67 IU/ml FSH based on the ELISA activity of the test samples, which included the FSH standard sample (positive control), the recombinant hFSH, human urine FSH and the recombinant hFSH-Fc fusion protein. Female Wistar rats of 19 to 28 days old could be used, however, one experiment was required for those rats within which the age difference was no more than 3 days and the weight difference was no more than 10 g to minimize the experimental variation. The 24 rats were equally divided into four groups for the following samples: FSH standard sample (positive control), the recombinant hFSH (commercial product), human urine FSH and the recombinant hFSH-Fc fusion protein. Each group was injected with corresponding samples above subcutaneously at the same time every day, two times a day, 0.2 mL each time for 3 consecutive days. 24 hours after the last injection, animals were killed in accordance with the sequence of administration by cervical vertebra dislocation, and their ovaries were dissected and weighed after drying the surfaces. The in vivo bioactivity of the recombinant hFSH, human urine hFSH and the recombinant hFSH-Fc was assayed by the parallel line quantitative analysis based on the ovarian weight gain of the standard group (positive control). The data showed the in vitro bioactivity of the recombinant hFSH-Fc, the recombinant hFSH and human urine FSH was 101,059,928 and 9321 IU/ml, respectively, and the in vivo bioactivity was 102,308,190 and 9051 IU/ml, respectively. These results indicated that, the recombinant hFSH-Fc fusion protein of the present disclosure had biological activity both in vitro and in vivo.

Figure 8:
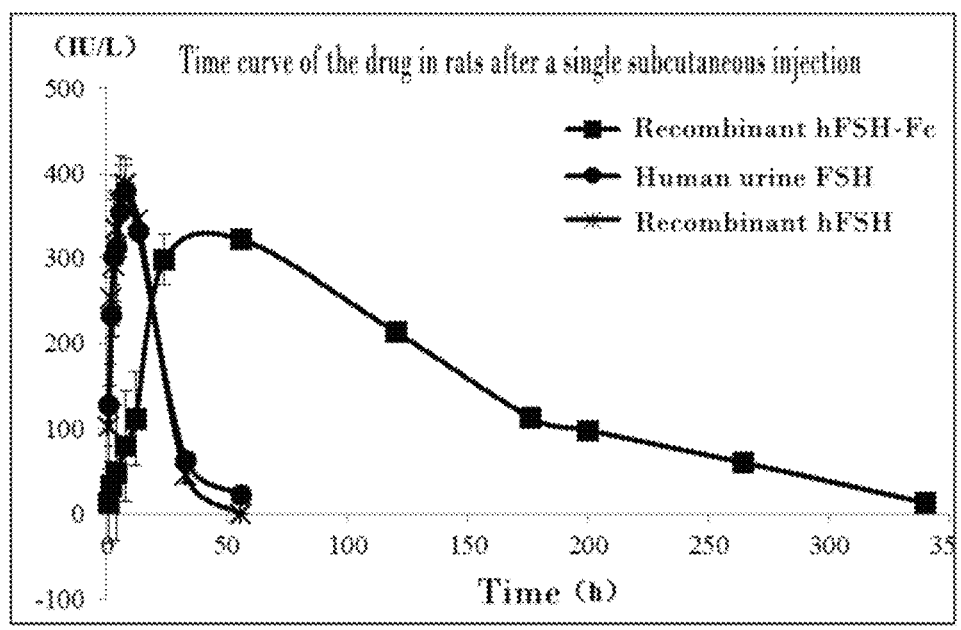
FIG. 8 shows the metabolic curve of the recombinant hFSH-Fc fusion protein, the recombinant hFSH and human urinary hFSH in rats.

Example 5. Pharmacokinetics of the Recombinant hFSH-Fc Fusion Protein 15 male Wistar rats with weight between 200-250 g were randomly and equally divided into 3 groups for the recombinant hFSH-Fc, human urine FSH and the recombinant hFSH. All groups were subcutaneously injected with corresponding protein with a single dose of 15 IU/kg. The blood samples were collected at different time intervals, i.e., at 1, 2, 3, 4, 6, 8, 12, 36, 56 h for the human urine FSH group and the recombinant hFSH group, at 1, 2, 4, 8, 12, 24, 56, 120, 176, 200, 264, 340 h for the recombinant hFSH-Fc group. The above samples were centrifuged at 3000 rpm for 5 min and the plasma supernatants were stored at −20° C. until assays were performed. The immunological activity of FSH in plasma at each time point was tested by ELISA kit (BIOCHECK, USA). The pharmacokinetic parameters were calculated by statistical method using PKSolver 2 software. The pharmacokinetic curves of each group were shown in FIG. 8, and the data of half-life was shown in Table 1. The results indicated that the half-life of the recombinant hFSH and human urine FSH in rats was 11.35±1.0 h and 12.7±2.8 h, respectively. The half-life of the recombinant hFSH-Fc fusion protein of the present disclosure was 47.24±13.92 h, which was at least 4 times longer than that of the recombinant hFSH and human urine FSH.

TABLE 1

The comparison of $T_{1/2}$

| Group | $T_{1/2}$ (h) |
|---|---|
| Recombinant hFSH-Fc | 47.24 ± 13.92 |
| Recombinant hFSH | 11.35 ± 1.0 |
| Human urine FSH | 12.7 ± 2.8 |

Example 6. Effect of the Recombinant hFSH-Fc Fusion Protein on Promoting Ovulation in Female Rats 90 female SD rats with weight between 200-250 g were fed and observed for more than 7 days in the experimental environment to ensure their healthy conditions. 60 of the healthy female SD rats were selected, randomly and equally divided into 4 groups: the negative control group, the recombinant hFSH-Fc fusion protein group, the recombinant hFSH group and the human urine FSH group. In addition, the weight distribution of rats in each group was similar. First, one estrous cycle of these rats was observed and monitored by vagina smear. Rats of the recombinant hFSH-Fc fusion protein group were subcutaneously injected with the corresponding drug (fusion protein) only one time on the first day among diestrous with a dose of 45 IU/kg per rat. Rats of the recombinant hFSH group and the human urine FSH group were subcutaneously injected with corresponding drug on the first day and the consecutive two days among diestrous (15 IU/kg/day) to give a total dose of 45 IU/kg per rat. Rats of the negative control group were subcutaneously injected with the same volume of normal saline. Rats of all groups were injected with HCG (10 IU per rat) subcutaneously on the fourth day (proestrus). On the fifth day (estrus), all rats were anesthetized, ovaries were dissected and weighed. The separated ovaries were fixed by Bouin's fluid and embedded in paraffin. Consecutive sections of the fixed ovary at 6 μm interval, microscopic organizational observation were performed, and the number of follicles was also recorded.

The number of follicles in each group was shown in Table 2. The results indicated that the recombinant hFSH-Fc fusion protein, the recombinant hFSH and human urine FSH could all promote the superovulation significantly (P<0.01) in female rats compared with the negative control group. Importantly, to achieve the equivalent efficacy, the recombinant hFSH-Fc fusion protein of the present disclosure needed to be administered just one time whereas both the recombinant hFSH and human urine FSH needed to be administered three times.

TABLE 2

Effect of recombinant hFSH-Fc fusion protein on promoting ovulation in female rats

| Group | n | Number of large follicles/section | Number of small follicles/section |
|---|---|---|---|
| Negative control | 15 | 8.2 ± 5.1 | 119.0 ± 36.1 |
| Recombinant hFSH-Fc | 15 | 24.3 ± 8.4$^a$ | 233.1 ± 65.9$^a$ |
| Recombinant hFSH | 15 | 21.1 ± 5.9$^a$ | 227.4 ± 55.2$^a$ |
| Human urine FSH | 15 | 20.4 ± 4.1$^a$ | 225.4 ± 31.6$^a$ |

Notes:
t test, compared with the negative control group,
$^a$p < 0.01.

Example 7. The Therapeutic Effect of the Recombinant hFSH-Fc Fusion Protein on Androgen Induced Anovulation in Female Rats 75 juvenile female SD rats of 9 days old were randomly divided into two groups: the normal control group (15 rats) and the animal model group (60 rats). Rats of the normal control group were subcutaneously injected once with 0.05 ml neutral tea-seed oil on the nape of neck, rats of the animal model group were subcutaneously injected once with 1.25 mg testosterone propionate on the nape of neck. Vagina was opened on the 70th day, and two cycles of consecutive vaginal smear (10 days in total as one cycle lasts for 5 days) were performed. The consecutive vaginal smear of the normal control group should show typical estrous cycle (proestrus, estrus, metestrus, diestrus), and any rat with abnormal estrous cycle was eliminated from the normal control group. The vaginal epithelial cells of the animal model group should be free of estrous cycle with sustained keratinization, indicating that the anovulatory rat model was successful, and any rat with abnormal performance was eliminated from the animal model group. On the 81th day and thereafter, 13 rats from the normal control group were injected subcutaneously with distilled water of 10 ml/kg/day. 52 rats from the anovulatory model mentioned above were randomly and equally divided into 4 groups: the negative control (animal model) group, the recombinant hFSH-Fc group, the recombinant hFSH group and the human urine FSH group. Rats of the negative control group were injected subcutaneously with distilled water of 10 ml/kg/day. Rats of the recombinant hFSH-Fc group were injected subcutaneously with hFSH-Fc of 45 IU/kg every three days, lasting for 15 days to give 5 injections in total. Rats of the recombinant hFSH group and the human urine FSH group were injected subcutaneously with corresponding drugs of 7.5 IU/kg twice a day, lasting for 15 days to give 30 injections in total. After the administration, continuous vaginal smears were collected from the rats in each group for two estrous cycles to examine their ovulation condition. Rats in each group were weighed and anesthetized by intraperitoneal injection with Urethan before the estrous cycle. The left ovary and the tissue samples of the uterus were fixed in 10% neutral formaldehyde for pathorphological observation of ovary and uterus. Quantitative indexes of ovarian observation included the number of follicles at different stages, the number of corpus luteums, and the index of uterus observation was measured by the thickness of endometrial.

Table 3 showed the results of the estrous cycles in each group, table 4 showed the results of the pathological changes of uterus and ovaries in each group. Compared with the negative control group, the recombinant hFSH-Fc fusion protein of the present disclosure, the recombinant hFSH and human urine FSH had a significant promoting effect on inducing estrus in anovulatory female rats, the number of large follicles and corpus luteums of these three latter groups were significantly higher ($P<0.01$) than those of the negative control group. However, both the recombinant hFSH and human urine FSH were required for 30 times administration in total and the recombinant hFSH-Fc fusion protein was only required for 5 times administration to achieve the same potency. The results showed that the recombinant hFSH-Fc fusion protein of the present disclosure, the recombinant hFSH and human urine FSH all had a significant promoting effect on inducing estrus in anovulatory female rats, but the dosing frequency of the fusion protein of the present disclosure was significantly less than that of the recombinant hFSH and human urine FSH.

TABLE 3

Promoting effect of recombinant hFSH-Fc fusion protein on inducing estrus in anovulatory female rats

| Group | Number of animals | Animals with estrous cycles | Ovulation rate |
| --- | --- | --- | --- |
| Normal control | 13 | 13 | 100 |
| Negative control | 13 | 0 | 0 |
| Recombinant hFSH-Fc | 13 | 10$^a$ | 76.9%$^a$ |
| Recombinant hFSH | 13 | 8$^a$ | 71.5%$^a$ |
| Human urine FSH | 13 | 6$^a$ | 70.2%$^a$ |

Notes:
$\chi^2$ test, compared with the negative control group,
$^a p < 0.01$.

TABLE 4

Pathological changes of uterus and ovaries in anovulatory female rats

| Group | Number of large follicles | Number of corpus luteums | Endometrial thickness (mm) |
| --- | --- | --- | --- |
| Normal control | 8.9 ± 3.3 | 6.1 ± 1.2 | 0.44 ± 0.15 |
| Negative control | 2.1 ± 0.6 | 0.4 ± 0.2 | 0.39 ± 0.14 |
| Recombinant hFSH-Fc | 7.7 ± 2.6$^a$ | 6.2 ± 2.3$^a$ | 0.42 ± 0.11 |
| Recombinant hFSH | 6.8 ± 1.8$^a$ | 5.8 ± 2.1$^a$ | 0.42 ± 0.08 |
| Human urine FSH | 6.7 ± 1.1$^a$ | 5.2 ± 1.4$^a$ | 0.41 ± 0.15 |

Notes:
t test, compared with the negative control group,
$^a p < 0.01$.

Example 8. Effect of the Recombinant hFSH-Fc Fusion Protein on Ovarian Stimulation in Rats 40 female Wistar rats of 22 days old were randomly and equally divided into 4 groups: the saline buffer (negative control) group, the recombinant hFSH-Fc fusion protein group, the recombinant hFSH (positive control) group, the human urine FSH group. The last three groups of rats were daily injected subcutaneously for consecutive four days with the corresponding protein (10 IU/day/rat) of the recombinant hFSH-Fc fusion protein, the recombinant hFSH and human urine FSH. At 26 day-old, these three groups were injected subcutaneously with 30 IU HCG. For the negative control group, the 22 to 26 day-old rats were daily injected subcutaneously with the same volume of saline buffer. At 28 day-old, rats of all four groups were injected with 0.1 ml of 1% Blue Evans (EB, Sigma) for 30 minutes staining. All rats were then killed by cervical vertebra luxation and the abdominal cavities were cut open to observe whether there was ascites. The rats with little or no ascites were injected intraperitoneally with 5 ml of saline, and the perfusate was collected and diluted to 10 ml in a test tube. Then, 0.05 ml of 0.1 M NaOH solution was added to the test tube and centrifuged for 10 minutes at 3000 rpm at room temperature. Spectrophotometer was used to determine the OD at 600 nm. Finally, the ovaries of both sides were dissected and weighed by electronic balance immediately. Observation indexes included: (1) the permeability of abdominal capillary: the EB content of the peritoneal lavage fluid was calculated according to the standard curve plotted thereby; (2) ascites grading: grade 1: no ascites, grade 2: small amount of ascites, grade 3: medium amount of ascites, grade 4: large amount of ascites, grade 5: massive ascites or ascites overflew from the abdominal incision; (3) ovarian weight: according to the Golan's criteria for the diagnosis of ovarian hyperstimulation syndrome, ovarian hyperstimulation syndrome could be diagnosed only when all three criteria of ovarian volume increasing, the permeability of abdominal capillary increasing and ascites emerging were met together.

After 4 days administration of the protein samples in same dose, as shown in Table 5, the EB content and the ascites score of the recombinant hFSH-Fc group had no significant difference from that of the saline control group. However, in comparison with the saline control group, the ovarian weight of the recombinant hFSH-Fc group was significantly increased but no ovarian hyperstimulation syndrome was observed. In contrast, the EB content, the ovarian weight and the ascites score of the recombinant hFSH group and the human urine FSH group were significantly higher than that of the saline control group and the recombinant hFSH-Fc group, indicating that the recombinant hFSH and human urine FSH could cause ovarian hyperstimulation syndrome. These results demonstrated that the side effects of the recombinant hFSH-Fc was relatively less than that of the recombinant hFSH and human urine FSH, indicating the recombinant hFSH-Fc protein was safer for clinical application.

TABLE 5

Comparison of the ascites grading and the EB content in abdominal fluid and the ovary weight

| Group | Ascites grading | EB content in abdominal fluid (μg/ml) | Ovary weight (mg) |
|---|---|---|---|
| Saline control | 1.00 ± 0.00 | 0.52 ± 0.01 | 28 ± 3 |
| Recombinant hFSH-Fc | 1.17 ± 0.25 | 0.63 ± 0.22 | 117 ± 24[a] |
| Recombinant hFSH | 2.36 ± 0.31[ab] | 3.24 ± 0.33[ab] | 165 ± 23[ac] |
| Human urine FSH | 2.58 ± 0.46[ab] | 3.78 ± 0.28[ab] | 155 ± 24[ac] |

Notes:
t test, compared with the normal control group,
[a] $p < 0.01$; Compared with the hFSH-Fc group;
[b] $p < 0.01$,
[c] $p < 0.05$.

The invention claimed is:

1. A recombinant homodimeric hFSH-Fc fusion protein with an amino acid sequence sequentially comprising an hFSH β-subunit, CTP, hFSH α-subunit, a flexible peptide linker, and human IgG2 Fc variant, from N-terminal to C-terminal,
   wherein said human IgG2 Fc variant comprises a hinge with a Pro331Ser mutation, CH2, and CH3 domains; and
   wherein the amino acid sequence of the fusion protein is set forth in SEQ ID NO: 2.

2. The recombinant hFSH-Fc fusion protein of claim 1, wherein the nucleotide sequence encoding the fusion protein is set forth in SEQ ID NO: 1.

3. A pharmaceutical composition, wherein the composition comprises a pharmaceutically acceptable carrier or excipient or diluent, and an effective amount of the recombinant hFSH-Fc fusion protein of claim 1.

4. A method for making the recombinant hFSH-Fc fusion protein of claim 1, comprising the following steps:
   (i) constructing an expression vector containing DNA encoding hFSH-Fc fusion protein, wherein the nucleotide sequence encoding the hFSH-Fc fusion protein is obtained by synthetic method, and is then inserted into a mammalian cell expression vector, leading to the expression plasmid containing hFSH-Fc fusion gene;
   (ii) stable expression of recombinant hFSH-Fc fusion protein in mammalian host cells, wherein the expression plasmid containing hFSH-Fc gene is transfected into a suitable mammalian host cell, and the stable cell lines with high expression level of the fusion protein are selected;
   (iii) culturing high density cell for the production of the fusion protein, wherein the stable cell line is transferred to a shake bottle or bioreactor to culture in a large scale, when the cell density reaches $1 \times 10^7$/mL, the culture temperature is reduced from 37° C. to 33° C., and then the cells are cultured at 33° C. until the cumulative protein production level no longer increases; and
   (iv) purifying the recombinant hFSH-Fc fusion protein comprising the steps of:
      a) Protein A affinity chromatography: centrifuge culture medium and collect the supernatant, according to the characteristic of the fusion protein coupled to an Fc fragment, use Protein A affinity chromatography to capture the target hFSH-Fc fusion protein, and
      b) hydrophobic chromatography: based on the hydrophobic characteristic of the recombinant hFSH-Fc fusion protein, use hydrophobic chromatography to further remove the impurities from the eluent of Protein A chromatography, the suitable resins for hydrophobic chromatography are selected from the following: Butyl Sepharose 4 Fast Flow, Octyl Sepharose 4 Fast Flow, Phenyl Sepharose 6 Fast Flow, Butyl-S Sepharose 6 Fast Flow, Butyl Sepharose 4B, Octyl Sepharose CL-4B and Phenyl Sepharose CL-4B.

5. The method for making the recombinant hFSH-Fc fusion protein of claim 4, wherein the mammalian cell expression vector of step (i) is pCDNA3, pCMV/ZEO, pIRES, pDR, pBK, pSPORT or pCMV-DHFR; the transfection methods of step (ii) includes phosphate calcium method, electroporation, liposome transfection and protoplast fusion; the mammalian host cell includes CHO, HEK293, COS, BHK, NSO and Sp2/0.

6. The method for making the recombinant hFSH-Fc fusion protein of claim 5, wherein the mammalian cell expression vector of step (i) is pCDNA3.

7. The method for making the recombinant hFSH-Fc fusion protein of claim 5, wherein the transfection method of step (ii) is electroporation.

8. The method for making the recombinant hFSH-Fc fusion protein of claim 5, wherein the mammalian host cell is CHO.

9. The method for making the recombinant hFSH-Fc fusion protein of claim 8, wherein the CHO cell is Dihydrofolate Reductase (DHFR) deficient CHO cells, which have been adapted to suspension culture in serum free medium (CHO DHFR).

10. The method for making the recombinant hFSH-Fc fusion protein of claim 4, wherein the optimization of cell culture conditions of step (iii) also include supplement of special additives to the culture medium.

11. The method for making the recombinant hFSH-Fc fusion protein of claim 10, wherein the supplement of special additives to the culture medium is adding 100 μM Cu2+ to the basic medium, adding 2 mM ManNAc (N-acetyl-D-amino mannose) to the feeding medium.

12. The method for making the recombinant hFSH-Fc fusion protein of claim 4, wherein the suitable resin for hydrophobic chromatography is Phenyl Sepharose 6 Fast Flow.

13. A method for treating human infertility in a subject thereof, comprising administering the recombinant hFSH-Fc fusion protein of claim 1.

* * * * *

SEQUENCE LISTING

<160> NUMBER OF SEQ ID NOS: 6

<210> SEQ ID NO 1
<211> LENGTH: 1482
<212> TYPE: DNA
<213> ORGANISM: Human

<400> SEQUENCE: 1

```
atgaagaccc tgcagttctt tttcctgttt tgctgttgga aggcaatctg ctgtaactca      60
tgtgagctga ctaatatcac cattgccatc gaaaaagagg aatgcaggtt ctgtattagt     120
atcaacacta cctggtgcgc tggctactgt tatacaaggg atctggtgta taaggaccca     180
gcacggccca aaatccagaa gacatgcact ttcaaagaac tggtgtacga gactgtgagg     240
gtccctggct gtgcccacca tgctgattcc ctgtacactt atccagtggc cacccagtgc     300
cactgtggaa agtgcgatag tgactcaaca gactgtactg tgcgaggcct gggaccttct     360
tactgcagtt ttggcgaaat gaaggagccc cgtttccagg attccagctc tagtaaagct     420 cccctcctt ccctgccctc accctcaaga ctgcctggac cttccgacac tcccatcctg     480
ccacaggccc ccgatgtgca ggactgccct gaatgtactc tgcaggagaa ccccttcttt     540
tctcagcccg gcgctcctat cctgcagtgt atgggatgct gttttagtag agcatatcct     600
accccactgc gctcaaagaa aacaatgctg gtccagaaga atgtgacaag cgaatctact     660
tgctgtgtgg ctaaatccta caaccgcgtg accgtgatgg gcggcttcaa ggtggagaat     720
cacacagcat gccattgttc tacttgctac taccataaga gtggatccgg tggcggttcc     780
ggtggaggcg gaagcggcgg tggaggatca gtggagtgcc ctccatgtcc agcacccct      840 gtcgcaggtc catctgtgtt cctgtttcca cccaagccta agacactct gatgatctcc      900 cgcacccag aagtcacctg tgtggtcgtg gatgtgagcc atgaagaccc cgaggtccag      960
ttcaattggt acgtggatgg cgtcgaggtg cacaacgcta agacaaaacc tagagaagag    1020
cagttcaact ctaccttcg cgtcgtgagt gtgctgacag tcgtgcacca ggactggctg    1080
aatggcaagg agtataagtg caaagtgagc aacaaaggac tgcctgcctc aatcgaaaag    1140
actatttcca agaccaaagg acagccaaga gagcccagg tgtacaccct gcctccaagc    1200
cgcgaagaga tgactaaaaa tcaggtctct ctgacctgtc tggtgaaggg gttttatcct    1260
```

```
agtgatatcg ccgtggaatg ggagtcaaac ggtcagccag agaacaatta caagaccaca    1320 cccctatgc tggacagcga tgggtctttc tttctgtata gcaaactgac agtggacaag    1380
tctcggtggc agcagggtaa cgtcttctct tgcagtgtga tgcacgaagc actgcacaat    1440
cattacaccc agaagtcact gtcactgagc ccaggaaaat ga                      1482
```

<210> SEQ ID NO 2
<211> LENGTH: 493
<212> TYPE: PRT
<213> ORGANISM: Human

<400> SEQUENCE: 2

```
Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Pro Arg Phe Gln Asp Ser Ser Ser Lys Ala Pro Pro Pro Ser
    130                 135                 140

Leu Pro Ser Pro Ser Arg Leu Pro Gly Pro Ser Asp Thr Pro Ile Leu
145                 150                 155                 160

Pro Gln Ala Pro Asp Val Gln Asp Cys Pro Glu Cys Thr Leu Gln Glu
                165                 170                 175

Asn Pro Phe Phe Ser Gln Pro Gly Ala Pro Ile Leu Gln Cys Met Gly
            180                 185                 190

Cys Cys Phe Ser Arg Ala Tyr Pro Thr Pro Leu Arg Ser Lys Lys Thr
        195                 200                 205

Met Leu Val Gln Lys Asn Val Thr Ser Glu Ser Thr Cys Cys Val Ala
    210                 215                 220

Lys Ser Tyr Asn Arg Val Thr Val Met Gly Gly Phe Lys Val Glu Asn
225                 230                 235                 240

His Thr Ala Cys His Cys Ser Thr Cys Tyr Tyr His Lys Ser Gly Ser
                245                 250                 255

Gly Gly Gly Ser Gly Gly Gly Ser Gly Gly Gly Ser Val Glu
            260                 265                 270

Cys Pro Pro Cys Pro Ala Pro Pro Val Ala Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Gln
305                 310                 315                 320

Phe Asn Trp Tyr Val Asp Gly Val Glu Val His Asn Ala Lys Thr Lys
                325                 330                 335
```

-continued

```
Pro Arg Glu Glu Gln Phe Asn Ser Thr Phe Arg Val Val Ser Val Leu
                340                 345                 350

Thr Val Val His Gln Asp Trp Leu Asn Gly Lys Glu Tyr Lys Cys Lys
            355                 360                 365

Val Ser Asn Lys Gly Leu Pro Ala Ser Ile Glu Lys Thr Ile Ser Lys
        370                 375                 380

Thr Lys Gly Gln Pro Arg Glu Pro Gln Val Tyr Thr Leu Pro Pro Ser
385                 390                 395                 400

Arg Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Met Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys
                485                 490

<210> SEQ ID NO 3
<211> LENGTH: 92
<212> TYPE: PRT
<213> ORGANISM: Human

<400> SEQUENCE: 3

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 4
<211> LENGTH: 33
<212> TYPE: PRT
<213> ORGANISM: Human

<400> SEQUENCE: 4

Pro Arg Phe Gln Asp Ser Ser Ser Ser Lys Ala Pro Pro Pro Ser Leu
1               5                   10                  15

Pro Ser Pro Ser Arg Leu Pro Gly Pro Ser Asp Thr Pro Ile Leu Pro
            20                  25                  30

Gln

<210> SEQ ID NO 5
<211> LENGTH: 111
<212> TYPE: PRT
<213> ORGANISM: Human
```

```
-continued

<400> SEQUENCE: 5

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
                20                  25                  30

Tyr Thr Arg Asp Leu Val Tyr Lys Asp Pro Ala Arg Pro Lys Ile Gln
            35                  40                  45

Lys Thr Cys Thr Phe Lys Glu Leu Val Tyr Glu Thr Val Arg Val Pro
        50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 6
<211> LENGTH: 48
<212> TYPE: PRT
<213> ORGANISM: Human

<400> SEQUENCE: 6

Gly Leu Tyr Ser Glu Arg Gly Leu Tyr Gly Leu Tyr Gly Leu Tyr Ser
1               5                   10                  15

Glu Arg Gly Leu Tyr Gly Leu Tyr Gly Leu Tyr Gly Leu Tyr Ser Glu
                20                  25                  30

Arg Gly Leu Tyr Gly Leu Tyr Gly Leu Tyr Gly Leu Tyr Ser Glu Arg
            35                  40                  45
```